United States Patent [19]

Navia

[11] Patent Number: 4,950,746

[45] Date of Patent: Aug. 21, 1990

[54] PROCESS FOR SYNTHESIZING SUCROSE DERIVATIVES BY REGIOSELECTIVE REACTION

[75] Inventor: Juan L. Navia, Athens, Ga.

[73] Assignee: Noramco, Inc., Atlanta, Ga.

[21] Appl. No.: 220,641

[22] Filed: Jul. 18, 1988

[51] Int. Cl.$^5$ .................. C07H 13/00; C07H 23/00; C08B 37/00; C07G 3/00

[52] U.S. Cl. .................. 536/119; 536/121; 536/115; 536/116; 536/120; 536/122; 536/124; 536/18.6; 536/4.1

[58] Field of Search .............. 536/119, 121, 115, 116, 536/120, 122, 124, 18.6, 4.1

[56] References Cited

U.S. PATENT DOCUMENTS

| | | | |
|---|---|---|---|
| 4,343,934 | 8/1982 | Jenner et al. | 536/122 |
| 4,362,869 | 12/1982 | Jenner et al. | 536/122 |
| 4,380,476 | 4/1983 | Mufti et al. | 127/46.3 |
| 4,435,440 | 3/1984 | Hough et al. | 426/658 |

OTHER PUBLICATIONS

Hassner, "Regiospecificity, A Useful Terminology in Addition and Elimination Reactions", J. Org. Chem., 33, No. 7, pp. 2684–2686, Jul. 1968.

David et al., "Regioselective Manipulation of Hydroxyl Groups Via Oranotin Derivatives", Tetrahedron, vol. 41, No. 4, pp. 643–663 (1985).

Wagner et al., "Preparation and Synthetic Utility of Some Organotin Derivatives of Nucleosides", J. Org. Chem., 39, 24 (1974).

Holzapfel et al., "Sucrose Derivatives and the Selective Benzoylation of the Secondary Hydroxyl Groups of 6, 1',6 -Tri-O-Tritylsucrose", S. Afr. Tydskr. Chem., 1984, 37(3), pp. 57–61.

Primary Examiner—Ronald W. Griffin
Assistant Examiner—Everett White
Attorney, Agent, or Firm—Charles J. Metz

[57] ABSTRACT

Sucrose is reacted with a 1,3-di(hydrocarbyloxy)-1,1,3,3-tetra(hydrocarbyl)distannoxane to produce a 1,3-di-(6-O-sucrose)-1,1,3,3-tetra(hydrocarbyl)distannoxane, which can be acylated to produce a sucross-6-ester.

49 Claims, 2 Drawing Sheets 4,950,746

PROCESS FOR SYNTHESIZING SUCROSE DERIVATIVES BY REGIOSELECTIVE REACTION

The invention relates to a process for producing sucrose derivatives by a regioselective reaction, and can be used, for instance, to produce mono-substituted sucrose derivatives wherein the substituent is in the 6 position. The invention also provides certain novel distannoxane compounds.

BACKGROUND OF THE INVENTION

Sucrose is a disaccharide whose molecular structure is shown as FIG. 1. (In the FIGURES showing the molecular structure of sucrose and derivatives thereof, the conformational formula is used. For convenience, the hydrogen atoms bonded to the carbon atoms in the two rings and the position numbers of the carbon atoms are shown only in FIG. 1.) The sucrose molecule contains three primary hydroxyl groups and five secondary hydroxyl groups. Therefore, when it is desired to prepare derivatives of sucrose involving reaction of the hydroxyl groups, it can be a major synthesis problem to direct the reaction only to the desired hydroxyl groups. For instance, the artificial sweetener 4,1', 6'-trichloro4,1', 6'-trideoxyoalactosucrose is derived from sucrose by replacing the hydroxyls in the 4, 1', and 6'positions with chlorine. (In the process of making the sweetener, the stereo configuration at the 4 position is reversed hence the compound is a galactosucrose.) This compound and methods for synthesizing it are disclosed in U.S. Pat. Nos. 4,343,934, 4,362,869, 4,380,476, and 4,435,440. The direction of the chlorine atoms to only the desired positions is a major synthesis problem, especially since the hydroxyls that are replaced are of differing reactivity (two are primary and one is secondary; the synthesis is further complicated by the fact that the primary hydroxyl in the 6 position is unsubstituted in the final product). The preparation of this sweetener is only one illustration of the synthesis of sucrose derivatives wherein it is desired either to derivatize certain specific hydroxyl groups, and only such hydroxyl groups, or to derivatize only a specified number of the hydroxyls, perhaps in this latter case without particular regard to which particular hydroxyl(s) are derivatized. The preparation of sucrose-based mono-ester surfactants is a commercial example of mono substitution on the sucrose molecule.

This invention provides a means for synthesizing sucrose compounds such as 6-substituted sucrose derivatives wherein the process of the invention is highly regioselective both with regard to directing the reaction strictly to the 6 position and to the preparation of monosubstituted derivatives only. The term "regioselective" refers to a reaction that highly favors a single major product. Ref., Hassner, "Regiospecificity. A Useful Terminology in Addition and Elimination Reactions", J. Org. Chem., 33. No. 7, 2684-6, July 1968.)

BRIEF SUMMARY OF THE INVENTION

The process of the invention comprises reacting sucrose with a 1,3-di(hydrocarbyloxy)-1,1,3,3-tetra(hydrocarbyl)distannoxane to produce a 1,3-di-(6-O-sucrose)-1,1,3,3tetra(hydrocarbyl)distannoxane, a new class of compounds, which can then be reacted with an acylating agent to produce a sucrose-6-ester. In a preferred aspect of the invention, the 1,3-di(hydrocarbyloxy)-1,1,3,3-tetra(hydrocarbyl)distannoxane reactant is generated in situ, for example, by reacting a di(hydrocarbyl)tin oxide or equivalent reactant with an alcohol or phenol.

THE PRIOR ART

In a review article entitled REGIOSELECTIVE MANIPULATION OF HYDROXYL GROUPS VIA ORGANOTIN DERIVATIVES, Tetrahedron, Vol. 41, No. 4, pp 643–663 (1985), David et al. disclose the reaction of tin compounds with hydroxyl-group containing compounds to produce stannoxyl compounds, which can then be alkylated or acylated to produce ethers or esters. The reaction of bis(tributyltin) oxide with various carbohydrates (including sucrose), followed by acylation to produce a mixture of esters of varying degrees of substitution, is disclosed. The use of dibutyltin oxide in a reaction with carbohydrates is also disclosed in the article. The authors report the preparation of two dialkylstannylene carbohydrate derivatives, the 2,3-0-dibutylstannylene derivative of methyl 4,6-O-benzylidene-α-D-glucopyranoside and 4,6-O-benzylidene-2,3-O-dibutylstannylene-α-D-mannopyranoside.

The proposed molecular structures of these two stannylene derivatives are shown in FIGS. 3 and 4 on page 645 of the article.

Wagner et al., J. Org. Chem., 39, 24 (1974), disclose the preparation of dibutylstannylene derivatives of nucleosides by reacting dibutyltin oxide with nucleosides in refluxing methanol. After stripping off the methanol, the stannylene derivative was acylated by reaction with equimolar quantities of acid chloride and triethylamine.

Holzapfel et al., in "Sucrose Derivatives and the Selective Benzoylation of the Secondary Hydroxyl groups of 6,1', 6'-tri-O-tritylsucrose", S. Afr. Tydskr. Chem, 1984,37(3), pages 57–61, disclose the reaction of dibutyltin oxide with 6,1', 6'-tri-O-tritylsucrose, followed by reaction with benzoyl chloride to produce a 72% yield of 3'-O-benzoyl-6,1', 6'-tri-O-tritylsucrose and 9% of the 2-O-benzoate derivative, and minor amounts of the 2,3'-dibenzoate derivative.

The basic teachings of the prior art (as represented by the above-cited authors) is that the reactivity of a hydroxyl group is increased by the formation of a bond with tin, but in polyhydroxylated compounds such as sugars it cannot be predicted a priori which hydroxyl group will be activated (see pages 646-7 of the cited David et al. paper, in the section entitled "Stereoelectronic consequences of the Sn-O bond. —nucleophilic enhancement of the oxygen atom", particularly the last paragraph of this section).

DETAILED DESCRIPTION OF THE INVENTION

The process of the invention comprises the reaction of a 1,3-di(hydrocarbyloxy)-1,1,3,3-tetra(hydrocarbyl)-distannoxane [which will be referred to for brevity as a "di(hydrocarbyloxy)distannoxane"]with sucrose to form a 1,3-di-(6-O-sucrose)-1,1,3,3-tetra(hydrocarbyl)-distannoxane [which will be referred to for brevity as a "di(hydrocarbyl)stannoxylsucrose"], which can then be reacted with an acylating agent to form a sucrose-6-ester. The two reactions will be illustrated with the following generalized experimental procedure in which dibutyltin oxide is used to generate the di(hydrocarbyloxy)distannoxane in situ, and benzoic anhydride is used as the acylating agent:

Methanol (100 ml), sucrose (5 gm), and dibutyltin oxide (3.64 gm - 1 molar equivalent, based on mols of sucrose - 1 mol of tin is used per mol of sucrose), are charged to a suitable reaction vessel. The contents of the reaction vessel are boiled under reflux for 2 to 2½hrs, after which the methanol is stripped off. The product of this reaction is 1,3-di-(6-O-sucrose)-1,1,3,3-tetrabutyldistannoxane (or dibutylstannoxylsucrose "DBSS"), a white solid. The white solid is taken up in N,N-dimethylformamide ("DMF"), 100 ml, and 3.64 gm of benzoic anhydride (about 1 molar equivalent, based on sucrose), is added. The contents of the reaction vessel are allowed to stand at room temperature overnight, after which the DMF is stripped off. Methylene chloride ("MeCl₂"), about 100 ml, is added. The product of the reaction, sucrose6-benzoate, is insoluble in MeCl₂, and it precipitates as a solid. The solid contains about 3-6 wt. % sucrose, with the balance being sucrose-6-benzoate. The reaction is almost perfectly regioselective in that the yield of sucrose benzoate substituted in the 6 position is greater than 97 percent. (The percentage is that part of the total peak area from an HPLC elution profile that is attributed to sucrose-6-benzoate. Other products are molecules that contain a UV chromophore that were not isolated or characterized. Compounds which are not UV-absorbers, most notably sucrose, are not detectable this way, so they are assayed and reported separately.) The organotin material remains in the MeCl₂; the sucrose-6-benzoate product contains not more than a trace of tin after the precipitation with MeCl₂.

In the specific illustrative reactions described above, dibutyltin oxide and sucrose were mixed and heated in refluxing methanol. It is believed that the methanol first reacts with the dibutyltin oxide to produce 1,3-dimethoxy-1,1,3,3-tetrabutyldistannoxane or "dimethoxydistannoxane"). The dimethoxydistannoxane is believed to be the species that reacts with the sucrose to form DBSS. Analysis of DBSS is consistent with the conclusion that DBSS is a compound of the structure:

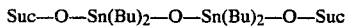

Figure 2:
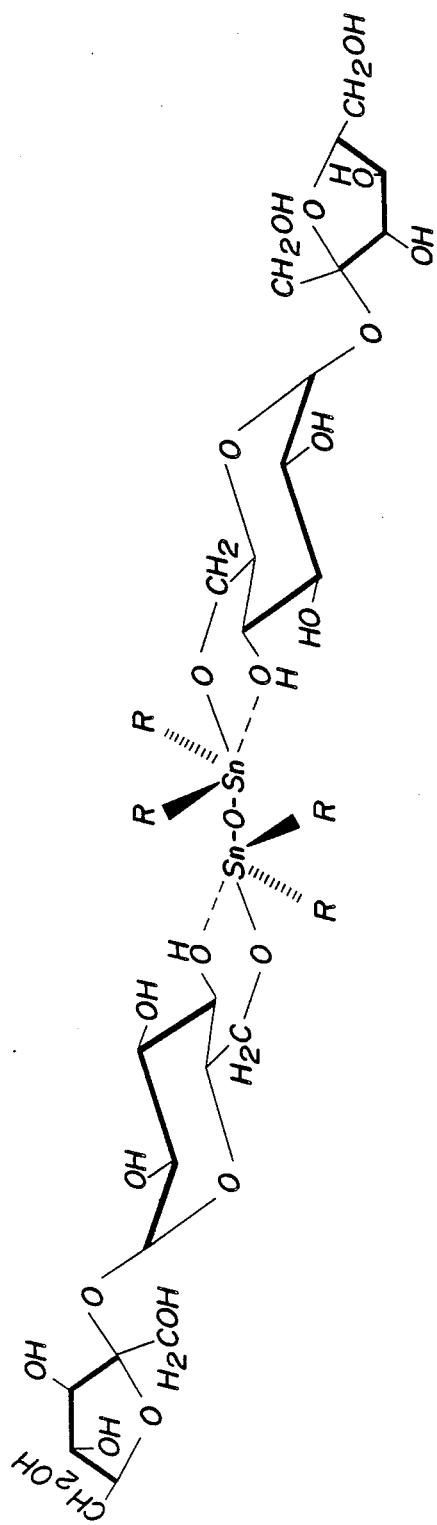

Suc—O—Sn(Bu)₂—O—Sn(Bu)₂—O—Suc wherein Suc represents 6-O-sucrose (i.e., the sucrose moiety is bonded through the oxygen that is bonded to the carbon atom in the 6 position) and wherein Bu represents butyl. FIG. 2 shows the molecular structure of the 1,3-di-(6-O-sucrose)-1,1,3,3-tetra(hydrocarbyl)distannoxanes that are produced by the process of the invention. In the FIGURE, the "R" groups represent hydrocarbyl groups, which can be the same or different.

The sucrose and di(hydrocarbyloxy)distannoxane reactants are used in proportions so as to produce the desired 1,3-di-(6-O-sucrose)-1,1,3,3-tetra(hydrocarbyl)-distannoxane product. In the preferred mode of carrying out the invention wherein the di(hydrocarbyloxy)-distannoxane is generated in situ by the reaction of a di(hydrocarbyl)tin oxide with a lower alkanol such as methanol, the di(hydrocarbyl)tin oxide and sucrose are preferably used in the reaction in proportions such that there is at least one mol of di(hydrocarbyl)tin oxide per mol of sucrose. Slightly higher proportions of the di(hydrocarbyl)tin oxide are not detrimental to the esterification reaction; however, less than equimolar proportions of the tin compound will decrease the amount of sucrose converted to DBSS and thereby reduce the specificity of the reaction.

In place of the dibutyltin oxide there can be used other di(hydrocarbyl)tin oxides in which the hydrocarbyl groups bonded to tin can be, individually, alkyl, cycloalkyl, aryl, or arylalkyl such as, for example, methyl, ethyl, propyl, butyl, octyl, benzyl, phenethyl, phenyl, naphthyl, cyclohexyl, and substituted phenyl. The preferred hydrocarbyl groups are alkyl having up to eight carbon atoms. In place of the tin oxide, a di(hydrocarbyl)tin dialkoxide, dihalide, diacylate, or other organic tin compound can be used as long as it generates the di(hydrocarbyloxy)distannoxane in situ.

The reaction is carried out in an organic liquid reaction medium that is a solvent for sucrose and the di(hydrocarbyloxy)distannoxane. When the di(hydrocarbyloxy)distannoxane is generated in situ, the reaction medium is preferably also a solvent for the compound(s) that are used to generate the di(hydrocarbyloxy)distannoxane. More preferably, the reaction medium is also one of the reactants that are used to generate the di(hydrocarbyloxy)distannoxane in situ. A wide variety of aliphatic and cycloaliphatic alcohols or phenols can be used as the reaction medium. It is often most economical to carry out the reaction between the di(hydrocarbyl)tin oxide (or equivalant reactant) and the alcohol or phenol under atmospheric reflux conditions. For this purpose, lower alkyl primary alcohols are generally preferred. Thus, the preferred reaction mediums are primary lower alkanols such as methanol, ethanol, n-propanol, n-butanol, n-pentanol, and n-hexanol. Additional alcohols and phenols that may be used as the reactant/reaction medium include secondary alcohols such as isopropyl alcohol and other secondary alkanols, phenol, substituted phenols such as lower alkyl-substituted phenols, cyclohexanol and substituted cyclohexanols such as lower alkyl-substituted cyclohexanol. Inert organic liquids such as toluene, xylene, and other hydrocarbons may also be used in the reaction, if desired. The di(hydrocarbyloxy)distannoxane can be represented by the formula:

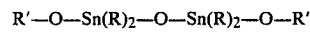

R'—O—Sn(R)₂—O—Sn(R)₂—O—R' wherein each R' individually represents alkyl, cycloalkyl, aryl, or aralkyl, and wherein each R individually represents a hydrocarbyl group, e.g., alkyl, cycloalkyl, aryl, or aralkyl.

The reaction between sucrose and the di(hydrocarbyloxy)distannoxane is carried out at a temperature and for a period of time sufficient to form the di(hydrocarbyl)stannoxylsucrose. Illustrative reaction temperatures are within the range of from about 50° to about 150° C. It is most convenient to carry out the reaction at the normal (i.e., at atmospheric pressure) refluxing temperature of the reaction medium. Illustrative reaction times are from about 1 to about 24 hours.

The di(hydrocarbyl)stannoxylsucrose is recovered by procedures that are analogous to those that are known in the art. The reaction medium is removed, as by stripping off, which may be performed under reduced pressure if desired. The product is a solid, which may be purified by recrystallization, if desired.

If desired, the di(hydrocarbyl)stannoxylsucrose product of the stripping procedure may be used directly without further purification in an acylation reaction. It is preferred to employ one molar equivalent of acylating agent in the reaction (the equivalence is based upon the molar equivalents of sucrose). In this context, one mol of benzoic anyhdride would constitute one molar equivalent. A slight excess, e.g., from 1 to 5 mol % excess, of acylating agent may be used, if desired.

The selection of the particular acylating agent to be used in the acylation reaction is dictated in part by the use to which the acylated product is to be put. For example, if the acyl group is being employed as a blocking group, as it would be in the preparation of the artificial sweetener as discussed above in the Background of the Invention section of this application, an acylating agent such as benzoic or acetic anhydride would be employed because it is inexpensive, the acyl group is readily removed at an appropriate stage of the synthesis, and it is stable to reactions that the acylated compound must undergo prior to removal of the acyl group. If a sucrose-6-ester is to be the ultimate product of the synthesis, then the acylating agent used is the one that will generate the desired acyl group for the ester product. With these principles in mind, among the acylating agents that can be used are the various anhydrides and acid halides of benzoic and substituted benzoic acid (e.g., 4-nitrobenzoic acid, 3,5-dinitrobenzoic acid, and the like), alkanoic acids such as acetic aCid, propionic acid, butyric acid, cyclohexanecarboxylic acid, long chain fatty acids, both saturated and unsaturated, such as stearic acid, oleic acid, linoleic acid, and the like, having up to, for example, 28 carbon atoms, unsaturated acids such as acrylic acid and methacrylic acid, substituted acids such chloroacetic acid, cyanoacetic acid, phenoxyacetic acid, and the like, and saturated and unsaturated dicarboxylic acids such as phthalic acid, maleic acid, glutaric acid, and the like.

The acylation reaction is carried out in an inert organic reaction vehicle such as DMF or other polar, aprotic compounds such as N-methylpyrrolidinone, dimethyl sulfoxide, and the like, that is a solvent for both reactants and reaction product. The acylation reaction is carried out at a temperature and for a period of time sufficient to prepare the sucrose-6-ester product. Typical reaction temperatures are found within the range of from about 0° C. to about 80° C. In the specific reaction discussed above, the reaction was carried out at room temperature (about 18-25° C.). Typical reaction times are usually found within the range of from about 0.5 hour to about 48 hours.

The sucrose-6-ester product of the above reaction can be recovered by procedures that are analogous to recovery procedures that are known in the art. For instance, the reaction medium may be removed (as by stripping), and the reaction products may then be taken up in a liquid material that dissolves either the sucrose-6-ester or the by-product tin compound(s), but not both. In the reaction illustrated above, methylene chloride was used because it completely dissolves the tin compound(s) but not the sucrose-6-ester. After adding the methylene chloride, the sucrose-6-ester is recovered by filtration. The sucrose-6-ester may be washed with moderately polar aprotic solvents such as acetonitrile or acetone to ensure essentially complete removal of the tin compound(s). Such solvents dissolve the tin compound(s), but little or no sucrose-6-ester.

Figure 1:
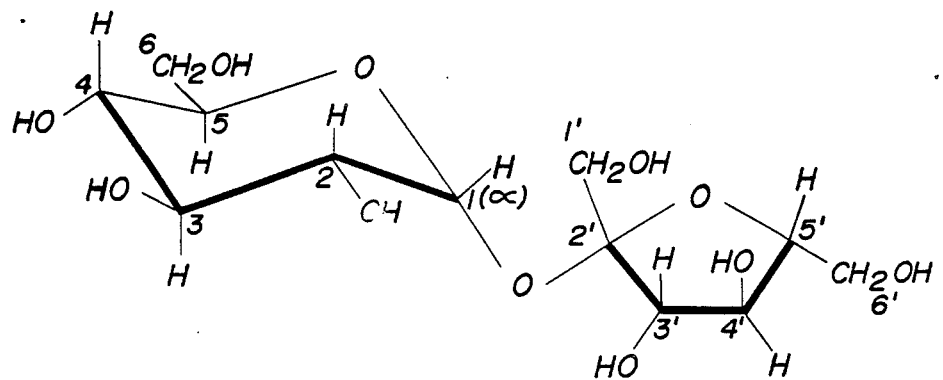
FIGS. 1-3 show structural formulas for sucrose, 1,3-di-(6-O-sucrose)-1,1,3,3-tetra(hydrocarbyl)distannoxane, and sucrose-6-esters, respectively.
Figure 3:
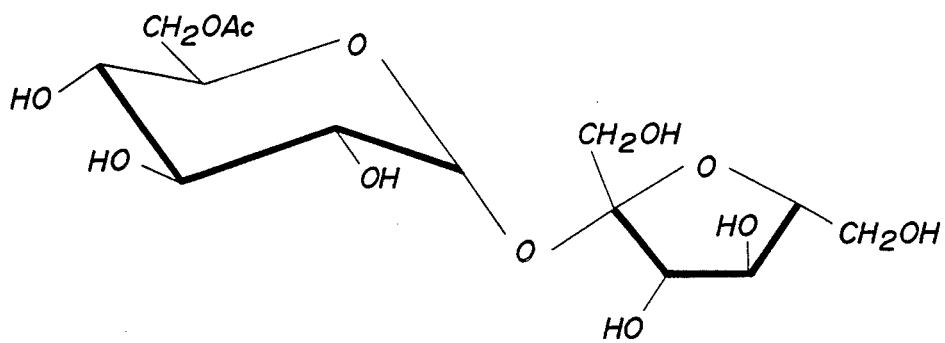

The molecular structure of the sucrose-6-ester product of invention is represented by the formula shown in FIG. 3, wherein "Ac" represents an acyl group.

If desired, the tin compound(s) may be recovered from methylene chloride solution and recycled. This adds to the economies of the process of the invention.

The invention is further illustrated by the examples set forth below.

EXAMPLE 1

1,3-Di-(6-O-sucrose)-1,1,3,3,-tetrabutyldistannoxane ("DBSS")

Sucrose (50 g) and dibutyltin oxide (38.2 g) were boiled in refluxing methanol (1 L) until a clear solution was obtained (2.5 hrs). The solution was evaporated, and the residue was dried under vacuum to give 87.9 g of DBSS.

Elemental analysis calculated for $C_{40}H_{78}O_{23}Sn_2$: C, 41.26; H, 6.75; Sn, 20.39. Found: C, 41.28; H, 6.84; Sn, 20.63.

EXAMPLE 2

Sucrose-6-benzoate

Method A.

A mixture of sucrose (5 g), dibutyltin oxide (3.64 g), and methanol (200 ml) was boiled under reflux until a transparent solution was obtained (about 2-2.5 hrs). The methanol was evaporated to dryness at 55-60° C. under diminished pressure with the aid of a water aspirator, and the residue taken up in DMF (100 ml). The clear, colorless solution was cooled to 0° C., benzoic anhydride (3.64 g) was added to the solution, and the mixture was stirred 4 hrs at 0-5° C., then stirred 48 hrs at ambient temperature. TLC (thin-layer chromatography) (15:10:1 $CHCl_3:CH_3OH:HOAc$) showed monobenzoates as the major product with traces of benzoic anhydride, sucrose dibenzoates, and sucrose still present. The mixture was evaporated to dryness at 35-40° C. with a mechanical pump to a colorless syrup which was dispersed in $MeCl_2$. A fine white solid precipitated from the $MeCl_2$ solution. It was recovered by vacuum filtration, washed first with $MeCl_2$ and then hexane, and then air-dried to give 4.97 g of a solid containing 5.1 wt. % sucrose (approx. 0.25 g), sucrose-6-benzoate (96.3% of all UV-absorbing material, no other sucrose monobenzoates were detected), and a trace of organotin compound(s). The methods used to analyze the products are set forth below.

ANALYTICAL METHODS

Sucrose benzoate samples were analyzed by high performance liquid chromatography (HPLC). Sample components were separated on a reversed-phase, octadecylsilane HPLC column, with gradient elution from 10% methanol/90% 0.01M $K_2HPO_4$, pH 7.5 buffer to 69.5% methanol/30.5% buffer. Detection was by ultraviolet absorption at 254 nm. Samples were analyzed against a sucrose-6-benzoate standard of known composition and purity to determine percentage by weight. (The sucrose-6-benzoate standard was prepared as described herein, recrystallized from acetonitrile to obtain a sample of high purity, and its structure was established by NMR analysis, which is given below.) Chromatographic purity was also calculated from the total chromatographic peak profile.

Sucrose laurates esters were analyzed on a reversed phase column using an isocratic mobile phase of 60% methanole/40% water. Refractive index detection was employed.

The sucrose content of sucrose benzoate samples was determined by HPLAC analysis. Sucrose was separated from the other sample components with an amine-bonded HPLC column, using an isocratic mobile phase of 85% acetonitrile/15% water. Refractive index detection was employed, and the sucrose peak in the sample was compared with that from a sucrose standard solution to allow quantitation of the sucrose content of the sample.

Sucrose-6-benzoate, NMR data:

| w (ppm) | ASSIGN-MENT | MULTIPLICITY | COUPLING CONSTANTS | (Hz) |
|---|---|---|---|---|
| 5.398 | H1 | d | J1,2 | 3.8 |
| 4.387 | H6a | dd | J5,6a | 2.3; |
|  |  |  | J6a,6b | 12.3 |
| 4.267 | H6b | dd | J5,6b | 5.2 |
| 4.206 | H3' | d | J3',4' | 8.6 |
| 4.05 | H5 | m |  |  |
| 4.016 | H4' | t | J4',5' | 8.5 |
| 3.88 | H5' | m |  |  |
| 3.756 | H3 | t | J2,3 = J3,4 | 10 |
| 3.565 | H2 | dd |  |  |
| 3.433 | H4 | t | J4,5 | 9.6 |

The NMR data was obtained at 270 MHz in $D_2O$ at ambient temperature. Chemical shifts are reported relative to tetramethylsilane at ($\delta$) 0 ppm (external reference).

Method B

DBSS (57.3 g) and benzoic anhydride (24.9 g) were stirred together in dimethylformamide (580 ml) at 18–22° C. for 23 hours. The mixture was evaporated to a syrup. A gummy mass was precipitated from the syrup by trituration with $MeCl_2$:hexane (2:1, 300 ml); the supernatant was decanted away and the gummy residue was triturated in $MeCl_2$ (160 ml), the solid was recovered by filtration, washed first with $MeCl_2$ and then hexane, and then air dried to give 36.2 g of product of which 71 wt % was sucrose-6-benzoate.

Method C.

Sucrose (50 g) and dibutyltin oxide (38.2 g) were boiled together in methanol (1 L) for 2.5 hr, then the solvent was evaporated and the residue was dried in vacuo. This material was benzoylated (benzoic anhydride, 38.2 g; DMF, 550 ml, at room temperature, overnight), the DMF was stripped and the syrupy residues dried further under vacuum. Addition of $MeCl_2$ (1 L) dissolved the dried mass and precipitated the crude product (44.5 g of which 3.4 wt % was sucrose and 86.6 wt % was sucrose-6-benzoate). A second crop of material precipitated during filtration and was also recovered (3.4 g; 1.6% sucrose; 89 wt-% sucrose-6-benzoate). The mother liquor was evaporated to a thin syrup, diluted with acetone to give a third crop (6.6 g; 0.44 wt-% sucrose; 100 wt-% sucrose-6-benzoate - this sample was apparently purer than the standard). The filtrate was evaporated and the resulting syrup was diluted with 95:5 acetonitrile:water. Tetrabutyldistannoxane dibenzoate (50 g) first oiled out, then crystallized. Evaporation of the filtrate and dilution with acetone gave an additional crop of sucrose-6-benzoate (7.2 g; 0.3 wt-% sucrose; 99 wt-% sucrose-6-benzoate).

EXAMPLE 3

USE OF DIOCTYLTIN OXIDE FOR THE CONVERSION OF SUCROSE TO SUCROSE-6BENZOATE

Sucrose (5 g) and dioctyltin oxide (5.3 g) were boiled together in 100 ml of refluxing methanol for 4 hours; toluene (100 ml) was added and the azeotrope was removed by distillation. (Water and methanol were removed as an azeotrope to drive the reaction to completion.) The remaining toluene was evaporated at 50–55° C. and the residue was dissolved in DMF (100 ml). Benzoic anhydride (3.64 g) was added to the solution. After 1 hr an additional 0.75 g of benzoic anhydride was added. After 3 hrs the mixture was evaporated; the residue was triturated (i.e., broken up) in $MeCl_2$ (100 ml); the resulting solid was filtered, washed with $MeCl_2$, and air-dried to give 6.85 g of crude sucrose-6-benzoate (11.2 wt-% sucrose; sucrose-6-benzoate is 90% of all UV absorbing material).

EXAMPLE 4

SUCROSE-6-ACETATE

DBSS (5 g) in DMF (50 ml) was treated with acetic anhydride (1.02 g) at room temperature for 3 hrs, then the mixture was evaporated and the syrup was triturated with 50 ml of $MeCl_2$. After 20 min the resulting solid was recovered by filtration, washed with $MeCl_2$ and hexane, and air-dried to give 3.1 g of product containing 63.4 wt % sucrose-6-acetate and 3.8 wt % sucrose.

EXAMPLE 5

SUCROSE-6-GLUTARATE

DBSS (5.73 g) in DMF (55 ml) was treated with glutaric anhydride (1.2 g) at room temperature for 3 hrs then at 40° C. (oil bath) overnight. Additional glutaric anhydride (1 g) was added, and after 4 hrs at 40° C. methanol (10–15 ml) was added to destroy unreacted anhydride. The mixture was allowed to remain at room temperature overnight, and was then evaporated. The resulting syrup was triturated with $MeCl_2$ (100 ml). The supernatant was decanted away, the process was repeated with two 80 ml portions of $MeCl_2$, and the hygroscopic solid was recovered by filtration and then vacuum drying to give 4.3 g of crude product.

EXAMPLE 6

SUCROSE-6-LAURATE

DBSS (5.73 g) was treated with lauric anhydride (3.9 g) in DMF (55 ml) at room temperature for 2 hrs and then at 40° C. (oil bath) for 5 hrs. The mixture was treated with additional lauric anhydride (1.1 g), and the reaction was continued for 2 hours and then quenched with methanol (10–15 ml) to destroy unreacted anhydride. The mixture was evaporated, and the residue was treated with a mixture containing 70 ml of diethyl ether and 100 ml hexane. The supernatant was decanted away from the resultant gel, and the gel was washed with three 100 ml portions of hexane, then dried under vacuum to give 4.08 g of a slightly hygroscopic material. HPLC analyses suggested that this product consisted of 60% sucrose-6-laurate, 13% sucrose, 20% mixed sucrose dilaurates, and 7% other sucrose monolaurates.

EXAMPLE 7

PREPARATION OF SUCROSE-6-BENZOATE USING DIBUTYLTIN OXIDE IN METHANOL

Sucrose (50.0 g, 1.00 mol equiv) and dibutyltin oxide (40.0 g, 1.10 mol equiv) were slurried in methanol (1000 ml) at reflux for 3 hours. After about 1 hour the solids had dissolved affording a clear colorless solution. The methanol was removed in vacuo with warming to 30°

C. to leave a white solid (89 g) of 1,3-di-(6-O-sucrose)1,1,3,3-tetrabutyldistannoxane (DBSS).

The DBSS was dissolved in DMF (150 ml) with warming to about 40° C. and the solution was cooled to ambient temperature. Benzoic anhydride (38.0 g, 1.15 mol equiv) was added and the resultant solution was stirred at room temperature for 3 hours at which time tlc (silica gel, eluant 15:10:2 chloroform:methanol:water) indicated the absence of benzoic anhydride and the presence of only a small amount of sucrose relative to sucrose monobenzoate. The DMF was evaporated at high vacuum to afford a pale greenish-yellow oil (approximately 160 g), which was dissolved in acetone (500 ml) at 40° C. and slowly cooled to room temperature. Sucrose-6-benzoate crystallized out as a white powder, which was stirred at 0° C. for 1 hour. The product was filtered, washed with acetone (2×50 ml), and dried in vacuo at ambient temperature for 16 hours. Yield 48.1 g. Assay: 88.1% sucrose-6-benzoate by HPLC.

EXAMPLE 8/METHOD A

PREPARATION OF SUCROSE-6-BENZOATE USING DIBUTYLTIN OXIDE IN BUTANOL

A 2000-ml, 3-neck, round-bottom flask, fitted with heating mantle, overhead stirrer, and Friedrich condenser topped with an argon inlet, was sequentially charged with 27.4 g (110 mmol) of dibutyltin oxide and 1250 ml of n-butanol. The slurry was heated to reflux with stirring over 0.5 hours, and the clear solution thus obtained was refluxed with stirring under argon for 2.5 hours. The reaction mixture was then allowed to cool to 90° C., and 34.2 g (100 mmol) of sucrose was added. This mixture was heated and stirred at 90° C. under argon for 4 hours, and the essentially clear solution thus produced was allowed to cool slowly to room temperature with stirring under argon. Evaporation of the solvent rotary evaporator, water aspirator vacuum, 40° C. bath temperature) followed by vacuum drying at 50° C. and 0.5 mm Hg for 8 hours produced 50.8 g (43.7 mmol) of DBSS.

The DBSS described above was dissolved in 400 ml of DMF and transferred to a 1000-ml, one-neck, round-bottom flask equipped with magnetic stir bar and argon inlet. The mixture was cooled in an ice bath, treated with 19.7 g (87.2 mmol) of benzoic anhydride, and allowed to warm and stir at room temperature for 12 hours under argon. Evaporation of the DMF (rotary evaporator, mechanical pump, 40° C. bath temperature) provided a viscous oil which was treated with 250 ml of acetone and heated to about 50° C. to produce a clear solution from which sucrose-6-benzoate readily crystallized on cooling to room temperature.

The product was filtered on a coarse-frit, sintered-glass filter, washed with acetone (2×100 ml), and vacuum dried (50° C., 0.5 mm, 16 hours) to produce 13.8 g of white solid shown by HPLC analysis to consists of 97.4% sucrose-6-benzoate.

EXAMPLE 8/METHOD B

PREPARATION OF SUCROSE-6-BENZOATE USING DIBUTYLTIN OXIDE IN BUTANOL

A 2000-ml, 3-neck, round-bottom flask, fitted with heating mantle, overhead stirrer, and Friedrich condenser topped with an argon inlet, was sequentially charged with 27.4 g (110 mmol) of dibutyltin oxide, 750 ml of n-butanol, and 500 ml of DMF. The slurry was heated to 125° C. with stirring over 0.5 hour, and the clear solution produced held at this temperature with stirring under argon for 2.5 hours. The reaction mixture was then allowed to cool to 90° C. and 34.2 g (100 mmol) of sucrose was added. This mixture was heated and stirred at 90° C. under argon for 4 hours, and the completely clear solution thus obtained was allowed to cool slowly to room temperature with stirring under argon. The reaction solvent was evaporated (rotary evaporator, water aspirator vacuum, 45° C. bath temperature), and the residual oil dissolved in 400 ml of DMF.

The DMF solution (50.0 mmol DBSS in theory) was transferred to a 1000-ml, one-neck, round-bottom flask equipped with magnetic stir bar and argon inlet. The solution was cooled in an ice bath, treated with 24.9 g (110 mmol) of benzoic anhydride, and stirred for 8 hours at 0° C. and then 12 hours at room temperature. The reaction was further processed as described in Example 8/Method A to provide 32.2 g of white solid shown by HPLC analysis to consist of 98.1% sucrose-6-benzoate.

EXAMPLE 9

PREPARATION OF SUCROSE-6-BENZOATE USING DIBUTYLTIN DIMETHOXIDE IN DMF

Sucrose (5.00 g, 1.00 mol equiv) was dissolved in DMF (20 ml) at 55° C. Dibutyltin dimethoxide (4.35 G, 1.01 mol equiv) was added and aspirator vacuum was applied. The mixture was stirred under vacuum for 1 hour, and then cooled to ambient temperature. (The dibutyltin dimethoxide reacts in situ with trace amounts of water to form 1,3-dimethoxy-1,1,3,3-tetrabutyldistannoxane.) Benzoic anhydride (4.00 g, 1 21 mol equiv) was added and the resultant solution was stirred at room temperature for 3 hours, at this time tlc (silica gel, eluant 15:10:2 chloroform:methanol:water) showed complete conversion to sucrose-6-benzoate. The DMF was evaporated at reduced pressure and the residue (15.8 g) dissolved in acetone (50 ml). Sucrose-6-benzoate crystallized on stirring at room temperature. The slurry was stirred for 48 hours at 0° C., filtered, and the product washed with acetone (2×20 ml) and dried in vacuo at 40° C. Yield 5.18 g. Assay: 96.3% sucrose-6-benzoate.

EXAMPLE 10

PREPARATION OF SUCROSE-6-BENZOATE USING DIBUTYLTIN OXIDE IN CYCLOHEXANOL

A 100-ml, one-neck, round-bottom flask, fitted with oil bath, magnetic stirrer, and condenser topped with an argon inlet, was sequentially charged with 2.49 g (10.0 mmol) of dibutyltin oxide, 50 ml of cyclohexanol, and 25 ml of o-xylene. The slurry was heated to 150° C. (bath) over 0.5 hour, and the clear solution thus obtained held at this temperature for an additional 1.5 hours. The heating bath was allowed to cool to 120° C. and the solution was treated with 3.42 g (10.0 mmol) of sucrose. After 6 hours at 120° C. (bath), the mixture was cooled to room temperature, the solvents evaporated (rotary evaporator, mechanical pump, 30° C. bath temperature), and the syrup thus obtained dissolved in 125 ml of DMF and treated with 2.26 g (10.0 mmol) of benzoic anhydride (room temperature, magnetic stirring, argon atmosphere, 6 hours). Evaporation of the DMF (rotary evaporator, mechanical pump, 40° C. bath temperature), followed by treatment with 100 ml of acetone, gave 2.82 g of light-tan solid shown by HPLC analysis to consist of 87.1% sucrose-6-benzoate.

EXAMPLE 11

PREPARATION OF SUCROSE-6-BENZOATE USING DIBUTYLTIN OXIDE AND PHENOL

Diphenoxydistannoxane was prepared according to the method of W. J. Considine, et al., *Can. J. Chem.*, 41, 1239 (1963). A 500-ml, one-neck, round-bottom flask, fitted with oil bath, magnetic stirrer, and Dean-Stark trap equipped with a Friedrich condenser topped with an argon inlet, was sequentially charged with 4.70 g (50.0 mmol) of phenol, 12.5 g (50.0 mmol) of dibutyltin oxide, and 350 ml of toluene. The slurry was stirred and heated to reflux, and the clear solution thus obtained refluxed for 3 hours during which time 150 ml of hazy (wet) toluene was removed from the Dean-Stark trap. The solution was allowed to cool to room temperature, evaporated (rotary evaporator, aspirator vacuum, 30° C. bath), and the off-white solid thus obtained dried in vacuo (room temperature, 0.25 mm of Hg, 3 hours).

The crude diphenoxydistannoxane (25.0 mmol in theory) was treated with 250 ml of DMF and 17.1 g (50.0 mmol) of sucrose and stirred at room temperature under argon. The sucrose was observed to rapidly dissolve, while the crude diphenoxydistannoxane was seen to require several hours to enter solution. After 12 hours, the essentially clear solution was treated with 11.3 g (50.0 mmol) of benzoic anhydride with continued stirring at room temperature under argon, and the progress of the benzoylation monitored by silica gel tlc (15:10:2, chloroform-methanol-water). After 12 additional hours, the excess benzoic anhydride was quenched with methanol (25 ml), the DMF removed (rotary evaporator, mechanical pump, 40° C. bath), and the crude product triturated with 200 ml of acetone to afford 19.35 g of white solid shown by HPLC analysis to consist of 88.0% sucrose-6-benzoate.

EXAMPLE 12

PREPARATION OF SUCROSE-6-BENZOATE USING DBSS AND BENZOYL CHLORIDE

A 100-ml, 3-neck, round-bottom flask, equipped with argon inlet, magnetic stir bar, thermometer, and addition funnel, was charged with 5.82 g (5.00 mmol) of DBSS, 25 ml of DMF, and 25 ml of diisopropylethylamine. This mixture was cooled to −10° C. treated dropwise with 4.36 g (31.0 mmol) of benzoyl chloride, and stirred for 60 min at about −10° C. After warming to room temperature and stirring for an additional 60 minutes, the reaction mixture was quenched with CH$_3$OH (15 ml), and evaporated (rotary evaporator, vaCuum pump, 55° C.) to a gummy solid shown by HPLC to contain 1.51 g of sucrose-6-benzoate.

The acylation reaction using an acid chloride, as illustrated here, works best using a hindered tertiary amine present in the reaction mixture as an acid acceptor. However, the reaction will proceed with no amine present or with a non-hindered tertiary amine (such as triethylamine) present.

EXAMPLE 13

PREPARATION OF SUCROSE-6-BENZOATE USING 1,3-DICHLORO-1,1,3,3-TETRABUTYLDISTANNOZANE

A 1000-ml, 3-neck, round-bottom flask, equipped with magnetic stir bar, oil bath, and argon inlet, was charged with 27.7 g (50.0 mmol) of 1,3-dichloro-1,1,3,3-tetrabutyldistannoxane (Aldrich Chemical Company, catalog #33,109–0) and 500 ml of DMF. After stirring for about 15 minutes under argon at room temperature, this solution was treated with 22.9 ml (21.6 g) of a 25 wt. % solution of sodium methoxide (5.40 g, 100 mmol) in methanol and stirring continued for 14.5 hours. The slurry was then treated with 35.9 g (105 mmol) of sucrose and heated for 19 hours in an 80° C. bath while argon was blown through the headspace of the reaction vessel to remove methanol.

After cooling to room temperature, the mixture was treated with 33.9 g (150 mmol) of benzoic anhydride with stirring at room temperature under argon for 96 hours. The reaction mixture was then evaporated (rotary evaporator, mechanical pump, 40° C.) to a syrup which was determined by HPLC analysis to contain 26.9 g of sucrose-6-benzoate.

This Example illustrates an alternative way to generate the dimethoxy distannoxane reactant in situ.

EXAMPLE 14

PREPARATION OF SUCROSE-6-BENZOATE USING DIBUTYLTIN OXIDE AND 2-ETHOXYETHANE

A slurry of dibutyltin oxide (7.36 g, 29.6 mmol) in 100 ml of toluene containing 2.76 g (29.6 mmol) of 2-ethoxyethanol was refluxed for 2 hours during which time the water produced (0.35 g) was collected in a Dean-Stark trap. The resulting clear solution was evaporated to give 10.43 g of a clear oil which was stirred for 2 hours at 50° C. with 10.0 g (29.2 mmol) of sucrose in 50 ml of DMF. After removal of about one-half the solvent (rotary evaporator, mechanical pump, 50° C. bath), the DBSS thus produced was treated at room temperature for 18 hours with 7.27 g (32.2 mmol) of benzoic anhydride in 20 ml of DMF. The solvent was then evaporated and the product worked up in the usual fashion with 100 ml of acetone to give 9.58 g of solid shown by HPLC analysis to contain 83.4% sucrose-6-benzoate.

This Example illustrates the use of a substituted alcohol to prepare the 1,3-di(hydrocarbyloxy)distannoxane reactant.

What is claimed is:

1. The process which comprises reacting sucrose with a 1,3-di(hydrocarbyloxy)-1,1,3,3-tetra(hydrocarbyl)distannoxane at a temperature and for a period of time sufficient to produce a 1,3-di-(6-O-sucrose)-1,1,3,3tetra(hydrocarbyl)distannoxane.

2. The process of claim 1 wherein the process is carried out in an alcohol or phenol reaction medium.

3. The process of claim 2 wherein the process is carried out in a lower alkanol reaction medium.

4. The process of claim 3 wherein the lower alkanol is methanol or butanol.

5. The process of claim 1 wherein the 1,3-di(hydrocarbyloxy)-1,1,3,3-tetra(hydrocarbyl)distannoxane is a 1,3-dialkoxy-1,1,3,3-tetra(hydrocarbyl)distannoxane or a 1,3-diphenoxy-1,1,3,3-tetra(hydrocarbyl)distannoxane.

6. The process of claim 1 wherein the 1,3-di(hydrocarbyloxy)-1,1,3,3-tetra(hydrocarbyl)distannoxane is a 1,3-dialkoxy-1,1,3,3-tetra(alkyl)distannoxane.

7. The process of claim 6 wherein the 1,3-di(hydrocarbyloxy)-1,1,3,3-tetra(alkyl)distannoxane is a 1,3-dimethoxy-1,1,3,3-tetra(alkyl)distannoxane or a 1,3-dibutoxy-1,1,3,3-tetra(alkyl)distannoxane.

8. The process of claim 7 wherein the said alkyl is butyl.

9. Process which comprises subjecting a mixture of (a) sucrose, (b) alcohol or phenol, and (c) a di(hydrocarbyl)tin oxide to a temperature and for a period of time sufficient to produce a 1,3-di-(6-O-sucrose)-1,1,3,3tetra(hydrocarbyl)distannoxane.

10. The process of claim 9 wherein said alcohol is a lower alkanol.

11. The process of claim 10 wherein the lower alkanol is methanol or butanol.

12. The process of claim 9 wherein the di(hydrocarbyl)tin oxide is a dialkyltin oxide.

13. The process of claim 9 wherein the di(hydrocarbyl)tin oxide is dibutyltin oxide.

14. The process of claim 10 wherein the di(hydrocarbyl)tin oxide is a dialkyltin oxide.

15. The process of claim 10 wherein the di(hydrocarbyl)tin oxide is dibutyltin oxide.

16. The process of claim 11 wherein the di(hydrocarbyl)tin oxide is a dialkyltin oxide.

17. The process of claim 11 wherein the di(hydrocarbyl)tin oxide is dibutyltin oxide.

18. The process which comprises the steps of:
(a) subjecting a mixture of sucrose, alcohol or phenol, and a di(hydrocarbyl)tin oxide to a temperature and for a period of time sufficient to produce a 1,3-di-(6-O-sucrose)-1,1,3,3-tetra(hydrocarbyl)-distannozane, and
(b) reacting the product of step (a) with an acylating agent to produce a sucrose-6-ester.

19. The process of claim 18 wherein said alcohol is a lower alkanol.

20. The process of claim 19 wherein said lower alkanol is methanol or butanol.

21. The process of claim 18 wherein the di(hydrocarbyl)tin oxide is a dialkyltin oxide.

22. The process of claim 18 wherein the di(hydrocarbyl)tin oxide is dibutyltin oxide.

23. The process of claim 18 wherein step (a) is carried out in refluxing alcohol.

24. The process of claim 18 wherein step (a) is carried out in refluxing lower alkanol.

25. The process of claim 18 wherein step (a) is carried out in refluxing methanol or butanol.

26. The process of claim 18 wherein the acylating agent is a carboxylic acid anhydride.

27. The process of claim 18 wherein the acylating agent is benzoic anhydride.

28. The process of claim 18 wherein the acylating agent is acetic anhydride.

29. The process of claim 19 wherein the acylating agent is a carboxylic acid anhydride.

30. The process of claim 19 wherein the acylating agent is benzoic anhydride.

31. The process of claim 19 wherein the acylating agent is acetic anhydride.

32. The process of claim 20 wherein the acylating agent is a carboxylic acid anhydride.

33. The process of claim 20 wherein the acylating agent is benzoic anhydride.

34. The process of claim 20 wherein the acylating agent is acetic anhydride.

35. The process of claim 21 wherein the acylating agent is a carboxylic acid anhydride.

36. The process of claim 21 wherein the acylating agent is benzoic anhydride.

37. The process of claim 21 wherein the acylating agent is acetic anhydride.

38. The process of claim 22 wherein the acylating agent is a carboxylic acid anhydride.

39. The process of claim 22 wherein the acylating agent is benzoic anhydride.

40. The process of claim 22 wherein the acylating agent is acetic anhydride.

41. The process of claim 1 wherein the 1,3-di-(6-O-sucrose)-1,1,3,3-tetra(hydrocarbyl)distannoxane product is subjected to a further step of reacting with an acylating agent to produce a sucrose-6-ester.

42. 1,3-Di-(6-O-sucrose)-1,1,3,3-tetra(hydrocarbyl)-distannoxane.

43. The compound of claim 42 wherein the hydrocarbyl is alkyl.

44. The compound of claim 43 wherein the alkyl is butyl.

45. The process of claim 18 wherein the acylating agent is a carboxylic acid chloride.

46. The process of claim 19 wherein the acylating agent is a carboxylic acid chloride.

47. The process of claim 20 wherein the acylating agent is a carboxylic acid chloride.

48. The process of claim 21 wherein the acylating agent is a carboxylic acid chloride.

49. The process of claim 22 wherein the acylating agent is a carboxylic acid chloride.

* * * * *